United States Patent [19]

Neumann

[11] 4,166,470

[45] Sep. 4, 1979

[54] EXTERNALLY CONTROLLED AND POWERED CARDIAC STIMULATING APPARATUS

[75] Inventor: Robert A. Neumann, Blaine, Minn.

[73] Assignee: Medtronic, Inc., Minneapolis, Minn.

[21] Appl. No.: 842,564

[22] Filed: Oct. 17, 1977

[51] Int. Cl.² .............................................. A61N 1/36
[52] U.S. Cl. ........................ 128/419 PG; 128/419 PS
[58] Field of Search ................. 128/419 PG, 421, 422, 128/423

[56] References Cited

U.S. PATENT DOCUMENTS

| Re. 28,003 | 5/1974 | Gobeli | 128/419 PG |
| 3,057,356 | 10/1962 | Greatbatch | 128/419 PG |
| 3,648,707 | 3/1972 | Greatbatch | 128/419 PG |
| 3,667,477 | 6/1972 | Susset et al. | 128/419 E |
| 3,747,604 | 7/1973 | Berkovits | 128/419 PG |
| 3,903,897 | 9/1975 | Woollons et al. | 128/419 PG |
| 3,911,929 | 10/1975 | Gobeli | 128/419 PG |
| 3,927,677 | 12/1975 | Gobeli | 128/419 PG |
| 3,999,556 | 12/1976 | Alferness | 128/419 PG |
| 3,999,557 | 12/1976 | Citron et al. | 128/419 PG |
| 4,041,954 | 8/1977 | Ohara | 128/419 PT |

FOREIGN PATENT DOCUMENTS 2520387 10/1978 Fed. Rep. of Germany .... 128/419 PG

OTHER PUBLICATIONS

Holcomb et al., "Medical and Biological Engineering", vol. 7, No. 5, Sep. 1969, pp. 493–499.
Holcomb et al., "21st ACEMB", Houston, Texas, Nov. 18–21, 1968, p. 22A1.

Primary Examiner—William E. Kamm
Attorney, Agent, or Firm—R. Lewis Gable; Joseph F. Breimayer

[57] ABSTRACT

Cardiac stimulating apparatus comprising a first external unit for transmitting electromagnetic energy within the patient's body to be received by a second, surgically implanted unit within the patient's body and adapted to be solely powered by the transmitted electromagnetic energy. The first external unit transmits a power signal and a control signal, the power signal comprising a first pulse for energizing the second internal unit, and the control signal for controlling the internal unit to pace the patient's heart in a variety of modes, e.g., atrial, ventricular and atrial/ventricular sequential pacing.

5 Claims, 7 Drawing Figures

EXTERNALLY CONTROLLED AND POWERED CARDIAC STIMULATING APPARATUS

BACKGROUND OF THE INVENTION

1. Field of the Invention

This invention relates to electronic devices implantable within the human body and in particular to cardiac monitoring and stimulating apparatus.

2. Description of the Prior Art

Heart pacemakers such as that described in U.S. Pat. No. 3,057,356 issued in the name of Wilson Greatbatch and assigned to the assignee of this invention, are known for providing electrical stimulus to the heart, whereby it is contracted at a desired rate in the order of 72 beats per minute. Such a heart pacemaker is capable of being implanted in the human body and operative in such an environment for relatively long periods of time. Typically, such pacemakers are implanted within the chest beneath the patient's skin and above the pectoral muscles or in the abdominal region by a surgical procedure wherein an incision is made in the selected region and the pacemaker is implanted within the patient's body. Such a pacemaker provides cardiac stimulation at low power levels by utilizing a small, completely implanted transistorized, battery-operated pacemaker connected via flexible electrode wires directly to the myocardium or heart muscle. The electrical stimulation provided by this pacemaker is provided at a fixed rate.

In an article by D. A. Nathan, S. Center, C. Y. Wu and W. Keller, "An Implantable Synchronous Pacemaker for the Long Term Correction of Complete Heart Block", *American Journal of Cardiology*, 11:362, there is described an implantable cardiac pacemaker whose rate is dependent upon the rate of the heart's natural pacemaker and which operates to detect the heart beat signal as derived from the auricular sensor electrode and, after a suitable delay and amplification, delivers a corresponding stimulus to the myocardium and in particular, the ventricle to initiate each heart contraction.

Such cardiac pacemakers, separately or in combination, tend to alleviate some examples of complete heart block. In a heart block, the normal electrical interconnection in the heart between its atrium and its ventricle is interrupted whereby the normal command signals directed by the atrium to the ventricle are interrupted with the ventricle contracting and expanding at its own intrinsic rate in the order of 30–40 beats per minute. Since the ventricle serves to pump the greater portion of blood through the arterial system, such a low rate does not provide sufficient blood supply. In normal heart operation, there is a natural sequence between the atrial contraction and the ventricular contraction, one following the other. In heart block, there is an obstruction to the electrical signal due, perhaps, to a deterioration of the heart muscle or to scar tissue as a result of surgery, whereby a block in the nature of a high electrical impedance is imposed in the electrical flow from the atrium to the ventrical.

Where the heart block is not complete, the heart may periodically operate for a period of time thus competing for control with the stimulation provided by the artificial cardiac pacemaker. Potentially dangerous situations may arise when an electronic pacemaker stimulation falls into the "T" wave portion of each natural complete beat. As shown in FIG. 1, the "T" wave follows by about 0.2 seconds each major beat pulse (or "R" wave causing contraction of the ventricles of the heart). Within the "T" wave is a critical interval known as the "vulnerable period" and, in the case of a highly abnormal heart, a pacemaker impulse falling into this period can conceivably elicit bursts of tachylcardia or fibrillation, which are undesirable and may even lead to a fatal sequence of arrhythmias.

Cardiac pacemakers of the demand type are known in the prior art such as that disclosed by United Kingdom Pat. No. 826,766 which provides electrical pulses to stimulate the heart only in the absence of normal heartbeat. As disclosed, the heartbeat is sensed by an acoustical device disposed external of the patient's body, responding to the presence of a heartbeat to provide an inhibit signal defeating the generation of heart stimulating pulses by the pacemaker. In the absence of the patient's natural heartbeat, there is disclosed that the pacemaker generates pulses at a fixed frequency.

In U.S. Pat. No. Re. 28,003, of David H. Gobel, assigned to the assignee of this invention, there is disclosed an implantable demand cardiac pacemaker comprising an oscillator circuit for generating a series of periodic pulses to be applied via a stimulator electrode to the ventricle of the heart. The stimulator electrode is also used to sense the "R" wave of the heart, as derived from its ventricle to be applied to a sensing portion of the cardiac pacemaker wherein, if the sensed signal is above a predetermined threshold level, a corresponding output is applied to an oscillator circuit to inhibit the generation of the stimulator pulse and to reset the oscillator to initate timing a new period. The following patents, each assigned to the assignee of this invention, provide further examples of demand type heart pacemakers: U.S. Pat. No. 3,648,707 of Wilson Greatbatch; U.S. Pat. No. 3,911,929 of David H. Gobeli; U.S. Pat. No. 3,927,677 of David H. Gobeli et al; U.S. Pat. No. 3,999,556 of Clifton Alferness; and U.S. Pat. No. 3,999,557 of Paul Citron et al.

Demand type pacemakers are particularly adapted to be used in patients having known heart problems such as arrhythmias. For example, if such a patient's heart develops an arrhythmia, failing to beat or to beat at a rate lower than a desired minimum, the demand type pacemaker is activated to pace the patient's heart at the desired rate. Of particular interest to the subject invention, are those patients that have recently undergone heart surgery; typically, these patients are apt to develop any and all known arrhythmias in the immediate post-operative period. Current therapy for such patients involves the implanting at the time of surgery of cardiac leads with their electrodes connected to the patient's heart and the other ends of the leads being connected to an external pacemaker to provide pacing for arrhythmia management.

In addition, the same pacemaker leads that interconnect the internally planted electrodes and its external pacemaker, are also connected to an external monitoring unit for providing signals indicative of the patient's heart activity to the external monitoring unit. A significant advantage of such pacemaker leads is that they may be used for recording of direct epicardial electrograms, which provide high quality precision data as to the patient's heart activity. The study of such wave shapes, i.e., morphology, is an invaluable aid in a diagnosis of arrhythmias. In this regard, it is understood that a normal EKG having its electrodes attached to various portions of the patient's skin does not provide the high quality output signal for diagnosis of arrhythmias as is obtained by cardiac electrodes attached directly to a patient's heart. For example, the output signal as obtained from such directly attached electrodes has a bandwidth in the order of 500 Hz and a signal to noise ratio in the order of 40 to 1, with no more than 30 db frequency loss. Such a high quality EKG signal cannot be obtained from a standard EKG monitor as is attached only to the outer skin of the patient.

However, the use of pacemaker leads directed through the patient's skin presents certain problems. Typically, if the external leads are left in the patient for any length of time, e.g., 5 to 7 days, an infection may develop at the exit side of the leads, and the leads may be accidentally pulled with subsequent damage to the patient's heart. Further, such leads present micro and macro shock hazards to the patient. For example, there are small residual charges on many objects within a surgical environment and if the leads are accidentally exposed to such a charge, it will be applied via the leads to the patient's heart possibly inducing an arrhythmia therein. Further, relatively high voltage such as carried by an AC powerline are typically found in the operating room; the electrogram recording apparatus is so powered and the contemplated accidental contact of the external leads with such an AC powered line would have serious consequences for the patient. In addition, it is necessary to remove the cardiac leads approximately 5 to 7 days after their surgical implantation. Further, there is considerable electrical environmental noise within an intensive care unit where a post-operative cardiac patient would be placed. Illustratively, such noise results from fluorescent lights or other electrical equipment typically found in an intensive care unit and is capable of inducing millivolt signals into such cardiac leads of similar amplitude to those signals derived from the patient's heart. Thus, such environmental noise-induced signals may serve to inhibit the external pacemaker from pacing, even though the patient's heart may not be beating. Further, it is contemplated that after the surgical implantation of such demand pacemakers, that the connections of the atrial and ventrical leads to the external pacemaker may be reversed, with resulting pacer-induced arrhythmias.

the prior art has suggested artificial pacemakers having a transmitter or unit disposed externally of the patient's body and a receiver surgically implanted within the patient, having leads directly connected to the patient's heart. For example, in the West German Auslegeschrift No. 25 20 387, entitled *Testing Arrangement for Artificial Pacemakers,* there is described a pacemaker having an external transmitter for transmitting external energy by radio frequency (RF) waves to an internally planted unit for supplying electrical stimulation to the heart. Further, it is disclosed that the internally planted unit is capable of transmitting information to a monitoring device disposed externally of the patient's body, for indicating various characteristics of the pacemaker.

Further, in a pair of articles entitled "A Demand Radio Frequency Cardiac Pacemaker", by W. G. Holcomb et al, appearing in *Med. & Biol. Eng.,* Vol. VII, pp. 493–499, Pergamon Press, 1969, and "An Endocardio Demand (P&R) Radio Frequency Pacemaker", by W. G. Holcomb et al, appearing in the 21st *ACEMB,* page 22A1, November 18–21, 1968, there is described a demandpacemaker including an external transmitter 10' as shown in FIG. 2, labeled PRIOR ART, for generating an RF signal from its primary coil or antenna 16' to be received by a receiver 12' internally implanted within the patient's skin 14'. In addition, the receiver 12' in turn transmits heart activity in terms of the currents of the heart's "R" wave to synchronize the activity of a pulse generator 26 within the external transmitter 10'. As shown in FIG. 2, the receiver 12' includes two separate electronic circuits each sharing common leads connected to the pacemaker electrodes, which are surgically connected to the patient's heart. The first circuit, i.e., the EKG transmitter section, consists of a rectifying circuit of diodes D20–D23 for providing power to a transistor amplifier Q10, to which is applied the EKG signal; the amplified EKG signal is applied in turn to a coil 34'a for transmission to the transmitter 10'. The primary coil or antenna 16' receives and applies the EKG signal via a detector 30, to be amplified by an amplifier 30, which provides the indicated EKG signal to be analyzed upon a display not shown. The second electronic circuit of the receiver 12' is the stimulus receiver, which furnishes the stimulating pulse to the cardiac electrodes. In particular, the output of the pulse generator 26 of the transmitter 10' is applied via closed switch 24 to superimpose a high voltage pulse upon the output of the 2 MHz oscillator, which is subsequently amplified by amplifier 20 and applied via detector 18 to the antenna 16'. The high voltage pacemaker pulse as superimposed upon the RF carrier, is received by the coil 34'b and rectified by the diode D25 and the capacitor C25 to actuate an electronic switch primarily comprised of transistors Q12 and Q13, which are closed thereby to apply the high voltage pulse via FET Q11 to the pacemaker electrodes, the FET Q11 serving to regulate the current passing to the pacemaker electrodes. The transistors Q12 and Q13 are voltage-responsive and disconnect the coil 34'b from the pacemaker electrodes in the absence of the high voltage pacemaker pulse.

It is understood that the RF carrier as derived from the oscillator 22 is continuously applied to the coil 16'. The secondary coil 34'a receives a continuous RF wave from the primary coil 16'. An EKG signal is derived from the pacemaker electrodes and is applied to the base of the amplifier transistor Q10, which in turn provides a correspondingly varying load to the coil 34'a, whereby a corresponding voltage fluctuation is induced across the coil 16'. In other words, the voltage appearing across the coil 16' is amplitude modulated in accordance with the patient's heart activity or EKG signal. Though the circuitry shown in FIG. 2 provides a relatively simple circuit of energizing the receiver 12' implanted within the patient, the EKG signal as derived from the patient does not contain sufficient precision to provide a diagnostic quality display of the patient's EKG. Typically, to provide a diagnostic quality display of the patient's EKG it is necessary to transmit the EKG signal with a bandwidth of 100 Hz with a signal to noise ratio in the order of 40 to 1 and with no more than a 3 db frequency loss; the circuitry shown in FIG. 2 does not provide such quality primarily due to the amplitude modulation type of signal transmission, which is sensitive to the relative positions in terms of distance and angle of orientation between the coils 16' and 34'a. In this regard, if the distance or the angle between the axes of the coils 16' and 34'a vary due to the patient's movement, the amplitude of the signal as seen by the detector 18 also will vary. Thus, in an amplitude modulation system, this body movement will provide a distortion in the EKG signal detected. In addition, the extraneous noise to which such a pacemaker would be exposed such as radiation from fluorescent lights or AC power lines, as well as other extraneous artifacts, may appear as amplitude modulation to introduce further errors in the signal received from the transmitter 10'.

SUMMARY OF THE INVENTION

It is therefore an object of this invention to provide a cardiac stimulating device implantable within a patient capable of being energized from a power source external of the patient's body, and for applying stimulating signals to the atrial and ventrical of the patient's heart.

It is a further object of this invention to provide an artificial heart pacemaker comprised of an external transmitter or power source for transmitting by RF coupling to a receiver implanted within the patient and operative independent of a local battery by the RF signals transmitted from the transmitter to pace the patient's heart in a variety of modes.

In accordance with these and other objects of the invention, there is provided cardiac stimulating apparatus comprising an external device or transmitter for transmitting an electromagnetic signal to an internal unit or receiver disposed within the patient's body, whereby power is supplied to the internal unit. The internal unit is coupled by electrodes to the atrial and ventrical portions of the patient's heart for applying stimulating signals to first and second sites (e.g., the atria and ventricles) of the patient's heart. In particular, the internal unit is operative to stimulate the heart in varying modes of operation and includes decoder means responsive to encoded signals transmitted from the external unit for controlling the manner of heart stimulation. In one illustrative embodiment of this invention, the internal unit is operative in a first mode to provide stimulating pulses to the atrium of the patient's heart and in a second mode for providing stimulating pulses to the ventrical of the patient's heart. Further, the decoder means may be actuated to pace synchronously or demand pace the atrium or to asynchronously or demand pace the ventrical of the patient's heart, and further to sequentially pace the atrial and the ventrical with an adjustable delay between the application of pulses thereto.

DESCRIPTION OF THE DRAWINGS

These and other objects and advantages of the present invention will become more apparent by referring to the following detailed description and accompanying drawings, in which.

DESCRIPTION OF THE PREFERRED EMBODIMENT

Figure 3:
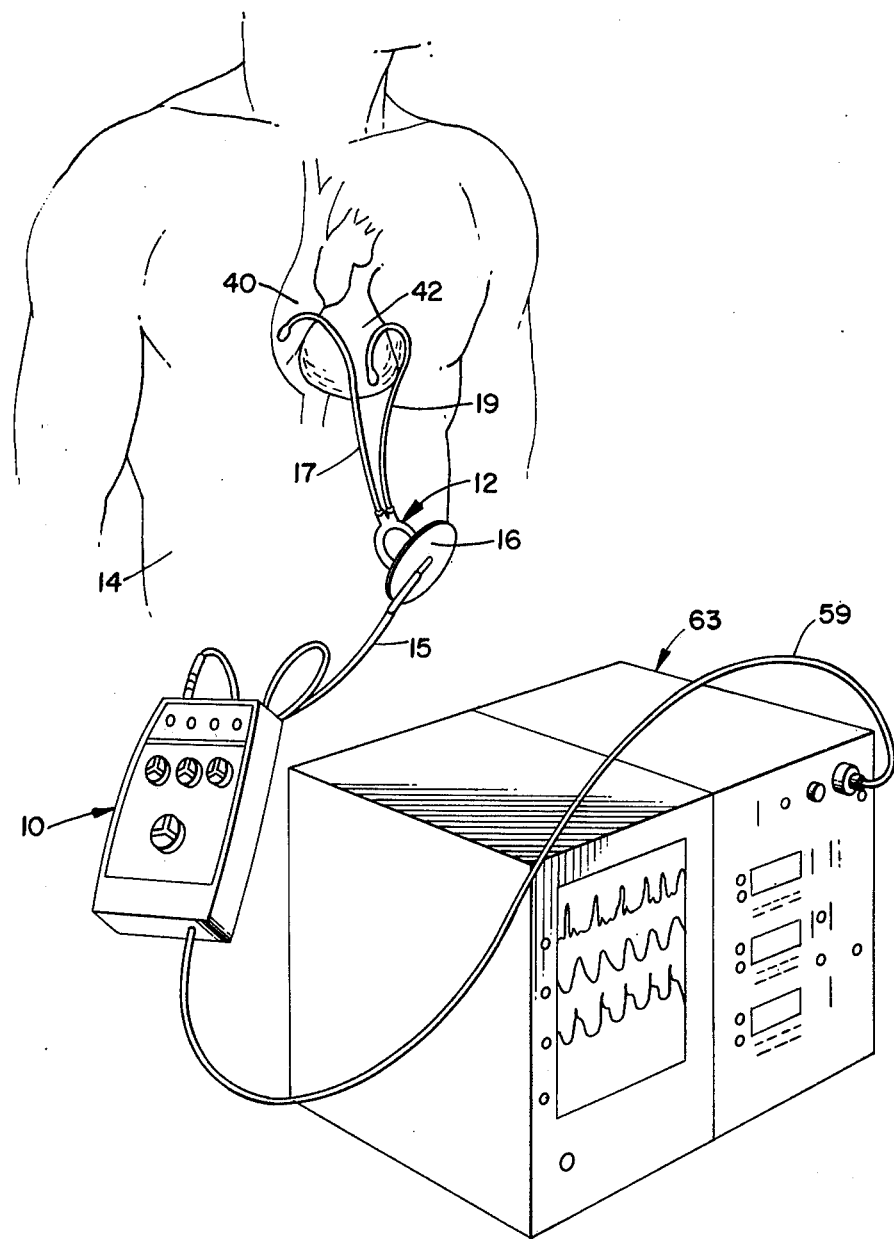
FIG. 3 is a pictorial showing of the manner in which an artificial heart pacemaker in accordance to the teachings of this invention, is implanted within the patient's body.
Figure 4:
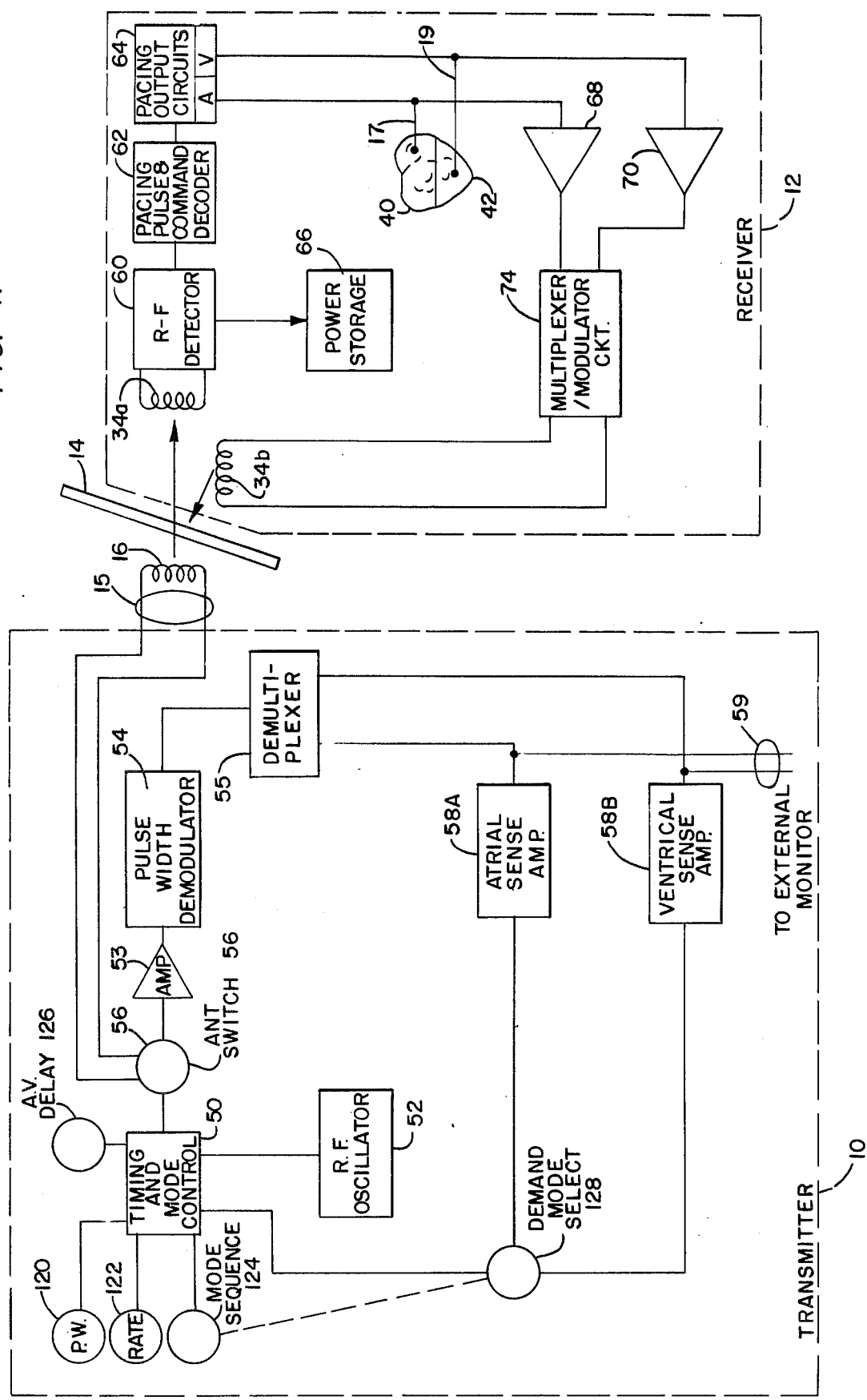
FIG. 4 is a block diagram of a transmitter or external unit and a receiver or internal unit in accordance with the teachings of this invention.

With regard to the drawings and in particular to FIG. 3, there is shown an artificial pacemaker and monitoring system in accordance with the teachings of this invention, including a transmitter or external unit 10 that generates stimulating pulses to be applied via a pair 15 of conductors to an incapsulated coil 16 whereby electromagnetic energy in the form of RF radiation is trammsitted through the skin 14 of the patient to be sensed by an internal unit 12 and in particular, as shown in FIG. 4, a coil 34a. The internal unit or receiver 12 is solely powered by the RF radiation transmitted to it for stimulating in various modes of operation the atrium 40 and ventrical 42 of the patient's heart, as by the leads 17 and 19, respectively.

Further, the external unit 10 is connected via conductor 59 to a monitoring unit 63, illustratively taking the form of a 78000 series unit of Hewlett-Packard for providing a display of the atrial and ventrical activity of the patient's heart.

With reference now to FIG. 4, there is shown the transmitter 10 including a timing and mode control 50 for controlling a variety of selected pacing functions and capable of operating in a demand or asynchronous mode for atrial, ventrical, or atrial-ventrical sequential pacing. In an illustrative embodiment of this invention, the control 50 may be appropriately adjusted to effect asynchronous atrial pacing from 50 to 800 BPM and demand atrial pacing from 50 to 180 BPM. It is contemplated that for use with postsurgical patients, arrhythmias may readily develop and by the application of heart stimulating pulses in the range of 180 to 800 BPM that the patient's heart may be forced out of its arrhythmic beating pattern. Further, the control 50 is adapted for asynchronous or demand ventrical pacing in the range of 50 to 180 BPM. In an atrial-ventrical sequential pacing mode, the control 50 may be adjusted to provide stimulation from 50 to 180 BPM with a delay between the atrial and ventrical pulses adjustable from 0 to 300 ms. The control 50 selectively applies the output of an R-F transmitter 52 by an antenna switch 56 via the set 15 of leads to the primary coil or antenna 16 for transmission of a corresponding electromagnetic wave to be received and detected by the receiving coil or antenna 34a.

Significantly, the transmitter or external unit 10 operates in first mode for effecting pacing and in a second mode for processing of EKG or electrograph information derived from the implanted receiver 12. In the second mode of operation, pulse width modulated data indicative of the amplitude of the heart's activity is transmitted from the coil or antenna 34b of the internal unit 12 to the coil 16 of the external unit 10 to be applied via the antenna switch 56 to a pulse-width demodulator 54 and a demultiplexer 55. As will be explained in detail later, the internal unit or receiver 12 is capable of sensing and monitoring the atrial and ventrical activity of the patient's heart and for transmitting pulse width modulated signals indicative thereof in timed sequence with a timing signal, to the transmitter or external unit 10. In this regard, the demodulator 54 and the demultiplexer 55 separates the atrial and ventrical signals transmitted from the internal unit 12, as well as demodulates the pulse width modulated signals to provide corresponding output signals indicative of the amplitude of the atrial and ventrical signals, via conductor 59 to the external monitoring device 63, as shown in FIG. 3, whereby a graphical display thereof may be provided with a diagnostic quality, so that the attending physician may accurately analyze the patient's heart activity. With such information, the physician is able to predict pending heart failure or arrhythmias. In this regard, the subject invention is capable of achieving diagnostic quality displays, i.e. is able to transmit to the receiver unit 10, heart signals with a bandwidth frequency of 100 Hz, a signal noise ratio in the order of 40 to 1 with no more than 3 db frequency loss. Further, a sensing amplifier 58 provides an inhibit signal to the control 50 whereby the control 50 is inhibited from operation during spontaneous cardiac activity.

As shown in FIG. 4, the receiver or internal unit 12 comprises an RF detector 60 for receiving the RF signal as derived from the input coil or antenna 34a, which separates the detected RF signal into power and control components, the power component energizing the power storage circuit 66. As will be explained in detail later with respect to FIG. 5, the power storage circuit 66 provides power for energizing the elements of the receiver 12. The RF detector 60 also provides a data signal to a pacing pulse and command decoder 62, which decodes the control signal transmitted from the transmitter 10 to detect the mode of pacing in which the receiver 12 is to be operated in and for applying energizing pulses to a pacing output circuit 64. As shown in FIGS. 4 and 3, the output of the pacing output circuit 64 is connected via leads 17 and 19 to the atrial and ventrical portions 40 and 42 of the patient's heart. In addition, the atrial and ventrical leads 17 and 19 are also connected to a monitoring or second portion of the internal unit 12, which comprises two operational amplifiers 68 and 70 for amplifying and applying respectively atrial and ventrical signals to a multiplexer-modulator circuit 74. As will be explained in detail with respect to FIG. 5, the circuit 74 operates to energize sequentially the coil or antenna 34b and thereby transmit via the coil 16 to the receiver 10 signals indicative of the atrial and ventrical activity of the patient's heart, accompanied by at least one timing signal. In addition, the circuit 74 modulates the ventrical and atrial signals in a manner that is not adversely effected by environmental noise, as occurs to amplitude modulated signals. In an illustrative embodiment of this invention, circuit 74 pulse width modulates each of the signals before transmitting same to the receiver 10. It is contemplated that the circuit 74 may also frequency modulate the atrial and ventrical signals to transmit them accurately to the external unit 10.

Figure 1:
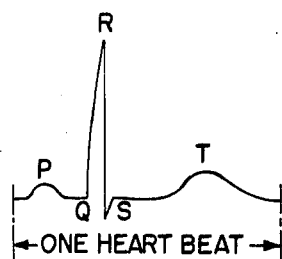
FIG. 1 illustrates the voltage wave produced by a human heart during one complete heartbeat.
Figure 2:
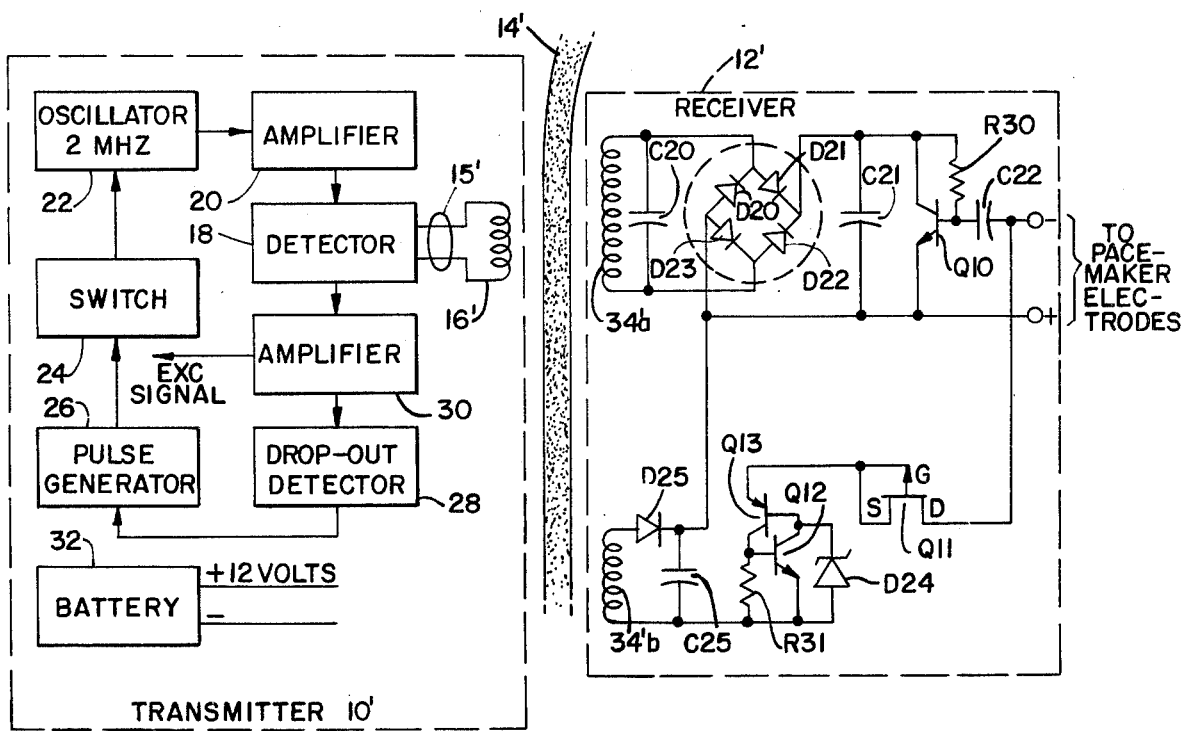
FIG. 2 is a schematic drawing above described of a demand heart pacemaker circuit of the prior art.
Figure 5:
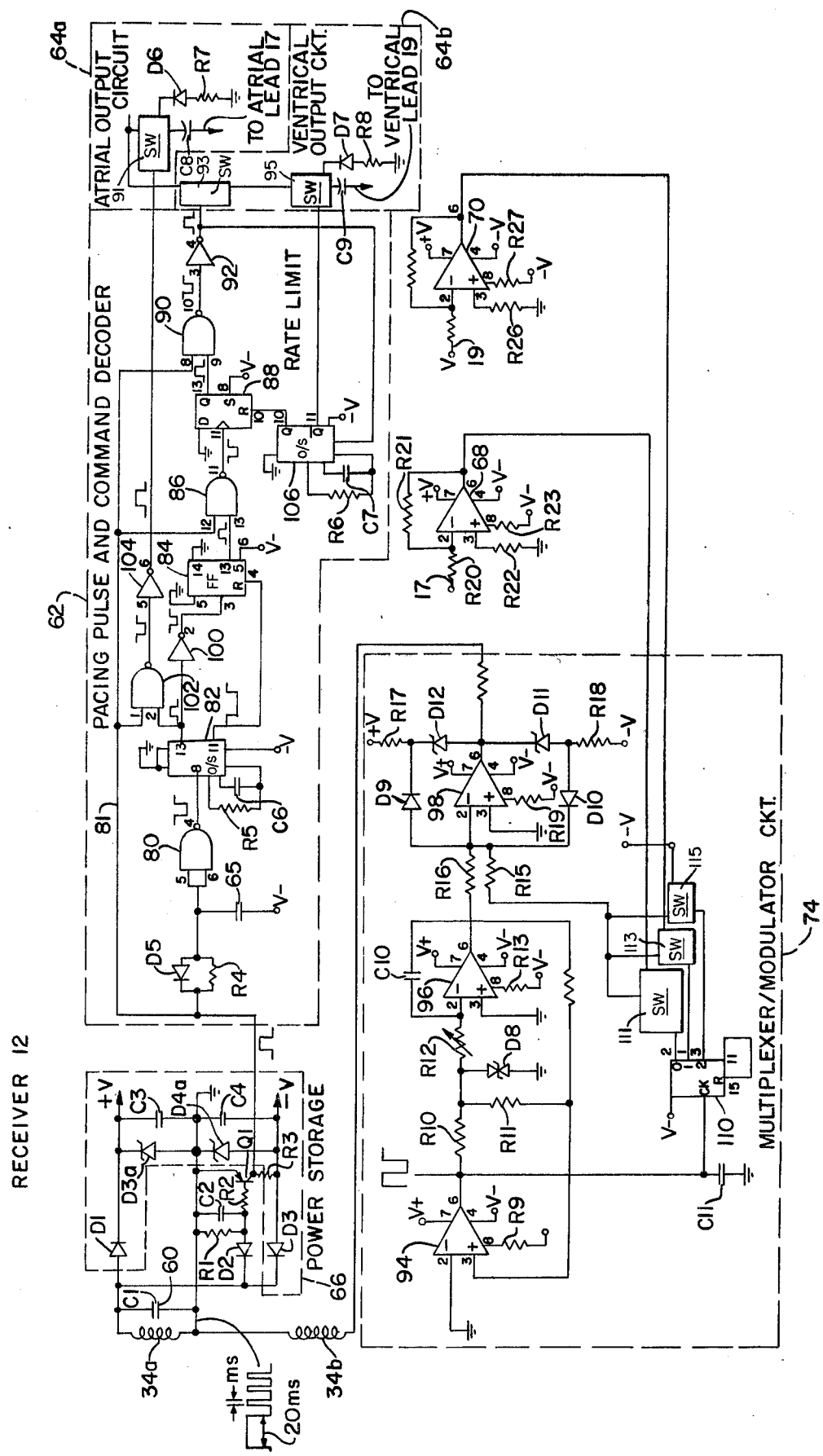
FIG. 5 is a detailed circuit diagram of the receiver as shown in FIGS. 3 and 4.

In FIG. 5, there is shown a detailed schematic diagram of the receiver 12 wherein the functional blocks as shown in FIG. 4, are shown and identified with similar numbers. The transmitter 10 transmits from its primary coil 16 to the secondary coil 34a an RF signal comprised of a train of amplitude modulated pulses. Each signal of such train comprises a first or power pulse that is stored in the power storage circuit 66 to provide energization for the elements of the receiver 12. The initial power pulse has a width in the order of at least 20 ms that is detected by the detector 60 in the form of a tuning capacitor C1 connected in parallel with the antenna or secondary coil 34a. A positive voltage derived from capacitor C1 is applied through a diode D1 to charge a capacitor C3 to a value determined by a zener diode D3a, illustratively a plus 10 volts. Further, a negative voltage is established through diode D3 to charge a capacitor C4 to a value limited by the zener diode D4a, illustratively a negative 10 volts. As a review of the schematic of FIG. 5 indicates, these negative and positive voltages energize the elements of the receiver 12 and are applied to various points throughout the receiver 12. Illustratively, the first power pulse has a pulse width in excess of 20 ms and an amplitude in excess of 30 volts (peak to peak), whereby the capacitors C3 and C4 are charged with a voltage that will not be discharged for a period in the order of 800 ms, which is long enough to permit the monitoring portion of the receiver 12 to pick up a P wave and an R wave, as shown in FIG. 1, of approximately 75 BPM. Further, the first power pulse is respectively derived from the control 50 of the external unit 10 once each 800 ms to continue the energization of the internal unit 12 to monitor the patient's heart. When the apparatus is operating in the telemetry mode only, the pulse width of the initial power pulse is increased to about 100 ms in a manner to be described. Similarly, during the transition period between the pacing and telemetry mode and during the refractory period of the patient's heart, a second power pulse, again of 100 ms length, is transmitted to power the receiver 12.

Further, as indicated in FIG. 5, the train of pulses also include a series of between 0 and 3 command pulses. If no command pulses are transmitted, the receiver 12 is commanded to operate in its monitoring mode and no pacing will be provided. If a single command pulse occurs within 2 ms after the initial power pulse, the pacing pulse and command decoder 62 decodes such instruction to cause the receiver 12 to pace the atrium at a pulse width equal to the width of the command pulse. If two pulses follow within 4 ms of the initial power pulse, the decoder 62 causes the receiver 12 to pace the atrium on the occurrence of the first command pulse, and to arm the ventricular output circuit 64b on the occurrence of the second command pulse. If there is a third command pulse occurring within a period of up to 300 ms of the trailing edge of the initial power pulse, the decoder 62 will effect a corresponding delayed actuation of the ventricular output circuit 64b to apply a pacing pulse to the patient's ventricle. By providing a variable delay before the occurrence of the ventricular pacing pulse, a sequential atrial-ventricular pacing mode can be effected.

The command pulses are derived from the capacitor C1 and applied to a detector circuit comprised of resistor R1 and capacitor C2 which responds only to the envelope of the power and command pulses, typically having a width in the order of 20 ms and 0.5 ms, respectively, to turn on transistor Q1, when a power or command pulse has been so detected. The voltage established upon capacitor C4 is coupled across resistor R3 and transistor Q1, whereby its output as derived from its collector is limited to a value less than that to which capacitor C4 is charged. As explained, the collector of transistor Q1 is turned on in response to power or command pulses, whereby positive going pulses of a duration correspondent to the power or command pulses are applied via a data line 81 to actuate the atrial and ventrical output circuits 64a and 64b in a manner to be explained.

Upon the occurrence of the initial power pulse, a corresponding negative going signal is developed at the collector of the nonconductive transistor Q1 and is applied via a diode D5 and resistor R4 connected in parallel and NAND gate 80 to set a one shot 82 upon the trailing edge of the initial power pulse. The resistor R4, a capacitor C5 and NAND gate 80 act as a discriminator to prevent the passage of any pulses shorter than approximately 20 ms, i.e., any command pulses. As a result, the one shot 82 only responds to the power pulse and derives at its output terminal 13 a timing pulse of approximately 2 ms commencing at the trailing edge of the initial power pulse and being applied to input terminal 2 of the NAND gate 102, thereby enabling the NAND gate 102 for a period of 2 ms. Thus, if a command pulse appears upon the data line 81 within this timing window of 2 ms after the trailing edge of the initial power pulse, an output is derived from the NAND gate 102 and inverted by digital inverter 104 to actuate the atrial output circuit 64a and in particular to render conductive switch 91, whereby a pacing pulse is applied via the lead 17 to stimulate the atrium 40 of the patient.

In addition, the 2 ms pulse derived from pin 13 of the one shot 82 is inverted by inverter 100 and is applied to input terminal 3 of flipflop 84, which responds to its trailing edge, that is, at the end of the window in which the atrial trailing pulse can be activated. The one shot 82 also generates at its output terminal a 4 ms negative pulse that is applied to the reset input terminal R of the flipflop 84, which in turn provides a positive output signal at its output Q following the termination of the output pulse derived from terminal 13 of one shot 82. This output pulse derived from flipflop 84 provides an enabling signal to the NAND gate 86, whereby the second, ventricular arming command pulse may be applied via the enabled NAND gate 86 to the input terminal 11 of a flipflop 88, which in turn applies a positive enabling signal from its output terminal 13 to a NAND gate 90. In this manner, a second window is defined illustratively in a period between 2 ms and 4 ms following the trailing edge of the first power pulse, in which window the second ventricular arming command pulse may appear to arm the ventricular output circuit 64b in preparation to be actuated by the third command pulse.

At this time, the NAND gate 90 is enabled or armed for a period illustratively up to 333 ms to wait the third, ventricular pacing command pulse on the data line 81 and applied to pin 8 of the NAND gate 90. If the third, ventricular pace command pulse occurs during the 333 ms window, it is passed via the enabled NAND gate 90, inverted by an inverter 92 to render conductive a switch 93 of the ventrical output circuit 64b, whereby a negative ventricular stimulating pulse is applied via the conductive switches 93 and 95, a capacitor C9 and lead 19 to energize the ventrical 42 of the patient's heart. The switches 91, 93, and 95 are well known in the art and may illustratively take the form of commercially available IC's.

As a further feature of this invention, the rate at which the patient's ventrical can be paced is limited to 180 ventricular BPM by the provision of a one shot 106. As seen in FIG. 5, the ventricular stimulating pulse as derived from the output of the inverter 92 is also applied to reset the one shot 106, which responds thereto by providing a one shot output pulse of a period of 333 ms from its output terminal 10 to be applied to the reset terminal R of the flipflop 88 for a corresponding period, whereby flipflop 88 may not be set to enable the above described ventrical pulse path (including NAND gate 90 and inverter 92) for a like period. In this manner, it is assured that the patient's ventricle 42 may not be paced at a rate above 180 BPM or more often than once each 333 ms, as may occur in the event of a failure of a circuit component.

Thus, depending on the coded signal transmitted to the internal unit 12, the artificial pacemaker is capable of operating to apply pacing pulses to either of the patient's atrium 40 or ventrical 42 or to operate in an atrial-ventrical sequential pacing mode, wherein the atrium 40 is first paced and after a selected time delay, the ventrical 42 is paced. In addition, if no pacing is desired, only the initial power pulse is applied, which provides a power energization for a subsequent period in which the remaining elements of the internal unit 12 remain energized, and a second monitoring portion of this circuit, as will now be described, is energized for transmitting to the external unit 10, atrial P-type and ventricular R-type waves as sensed by electrodes applied directly to the patient's heart. In the following, the monitoring portion of the receiver 12 is explained whereby the atrial and ventricular signals are time multiplexed and pulse width modulated, to provide a train of pulses energizing the coil 34b, to induce similar signals into the primary coil 16 of the external unit 10, whereby corresponding atrial and ventricular signals may be separated and applied to the external monitor 63, as shown in FIG. 3. During periods of RF transmission when the antenna switch 56 as shown in FIG. 4 is in a position to transmit only the RF transmission, the monitoring portion of the receiver 12 is not operative to transmit the atrial and ventricular signals, because the magnetic field created by the RF transmission from the coil 16 is of significantly greater magnitude than that of the atrial and ventricular signals emanating from the coil 34b.

As shown generally in FIG. 4 and in detail in FIG. 5, the electrodes connected to the atrium 40 and ventrical 42 of the patient's heart are connected by the leads 17 and 19 to operational amplifiers 68 and 70, whereby the atrial and ventricular signals are amplified and applied to the multiplexer/modulator circuit 74. In particular, the atrial and ventricular signals are applied to a time multiplexing portion of the circuit 74 for placing these signals in a desired time sequence, along with a timing signal. In particular, the circuit 74 comprises an operational amplifier 94 having internal feedback and operated as a free-running oscillator to provide a square wave output that is applied to a counter 110, from whose three output terminals are derived in sequence three timing signals, which are applied in turn to three corresponding switches 111, 113 and 115 sequentially enabling the three switches in a timed sequence. The switches 111, 113 and 115 may take the form of commercially available IC's. In particular, the output of the atrial operational amplifier 68 is applied to the switch 111, while the output of the ventricular operational amplifier 70 is applied to the switch 111. A negative voltage, as derived from the capacitor C3 is applied to the switch 115 to provide the desired timing signal. Thus, the multiplexer modifies the square wave output of the oscillator 94 to provide therefrom in sequence a first signal indicative of the atrial activity of the patient's heart, a second signal indicative of the ventricular activity of the patient's heart and a third positive going timing pulse to be applied to a pulse width modulating circuit essentially comprised of the operational amplifier 98.

In an illustrative embodiment of this invention, the three timing outputs of the counter 110 are 1.0 ms in width, occurring every 3 ms to thereby sample the P-wave signal appearing at the patient's atrium 40 or the R-wave signal appearing at the patient's ventrical 42. In the illustrative embodiment, the sampling frequency is 333 Hz. Thus, with the average P-wave signal lasting longer than 20 ms, the P-wave is sampled about six times as it rises and falls to provide about six sample amplitudes of signals to be applied to the amplifier 98. In similar fashion, a number of sampled amplitudes of the R-wave are derived and applied in sequence with the pulses indicative of instantaneous P-wave amplitudes to the amplifier 98. The instantaneous sampled amplitudes are transformed into pulse width modulated signals by amplifier 98.

In particular, the output of the square wave generator formed by the oscillator 94 is applied to a second free running oscillator 96, which in turn generates a triangle wave output to be applied via resistor R16 to a first input of the operational amplifier 98 acting as a comparator and pulse width modulator. A second input to be summed with the first, is derived via a resistor R15 from the commonly connected output electrodes of the switches 111, 113 and 115. Thus, when no signal is derived from either the atrial or ventricular amplifier 68 or 70, only the triangular output of the oscillator 96 is applied to the amplifier 98, which in turn produces a square wave output of a first fixed period indicating a zero amplitude signal. The output of the amplifier 98 is limited to fixed voltages set by the zener diodes D11 and D12, 3.3 volts illustratively. In addition, resistors R17 and R18 along with diodes D9 and D10 provide a source of power for the signals applied to the coil 34b, whereby the operational amplifier 98 is essentially used as a comparator or pulse width modulator and not a power amplifier.

The sampled amplitudes of the atrial and ventricular signals are summed with the triangular wave output derived from the oscillator 96. Summing these two voltages allows the rising triangular wave derived from the oscillator 96, to exceed the reference potential as applied to pin 3 of the amplifier 98, whereby the amplifier 98 is turned "on" earlier and "off" later in time, thus widening the output pulse of the amplifier 98. In this manner, each of the atrial and ventricular signals whose amplitude indicate the intensity of the corresponding atrial and ventrical heart activity, are sampled pulse-width modulated and applied as energizing signals to the coil 34b.

Thus, there is provided a three-phase timing or multiplexing function, whereby a first pulse-width modulated signal indicative of a signal appearing at the atrial electrode is provided, followed by a second, pulse-width modulated signal indicative of the signal appearing at the ventrical electrode, followed by a 100% positive indicating signal. The third phase signal is used as a timing reference, whereby the demodulator 54 within the transmitter 10 determines the presence of and demodulates the atrial and ventricular signals.

Figure 6:
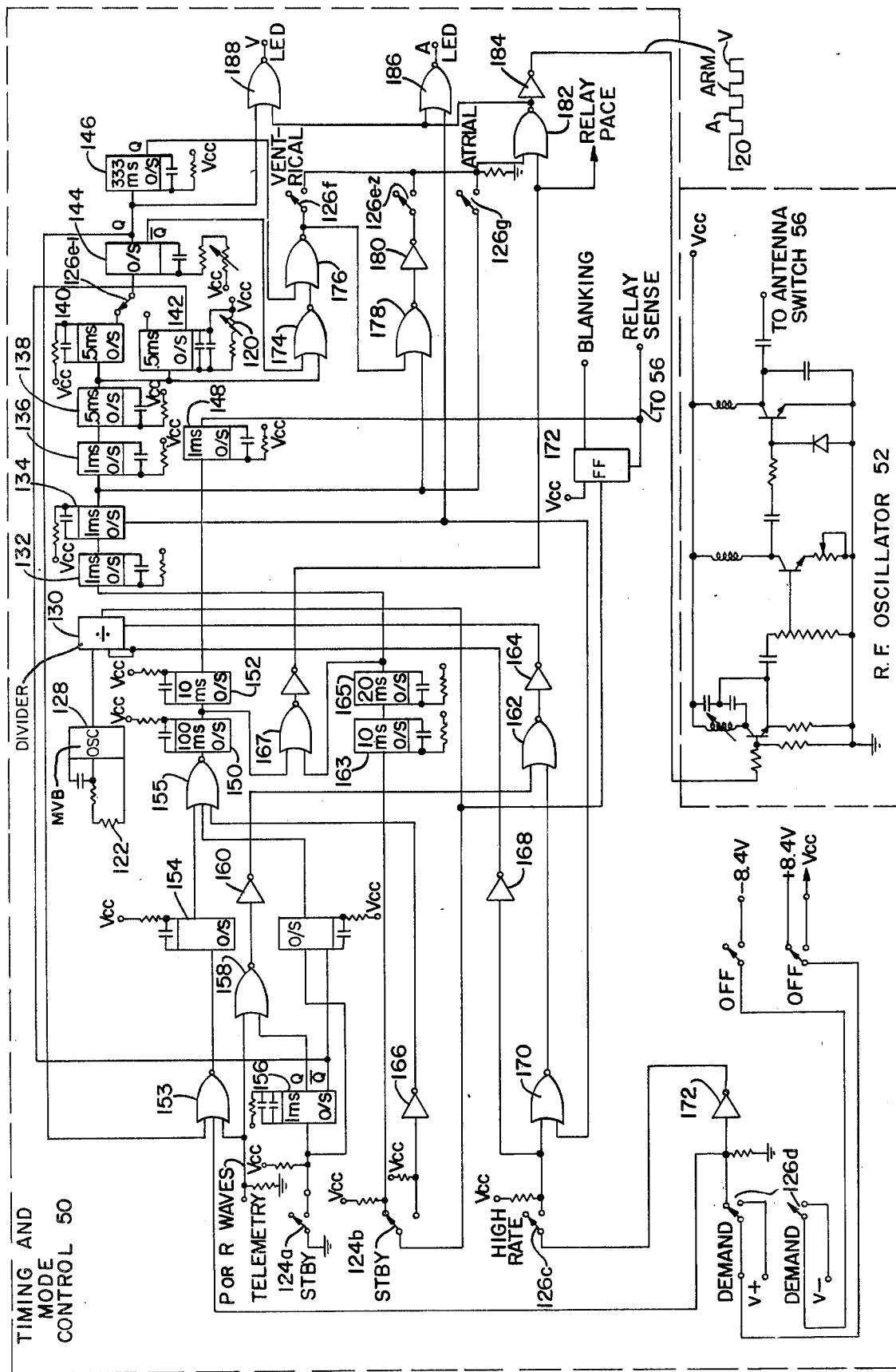
FIGS. 6 and 7 comprise a detailed circuit diagram of the transmitter as shown in FIGS. 3 and 4.

Referring now to FIG. 6, there is shown a detailed circuit diagram of the timing and mode control circuit 50 and the RF oscillator 52 of the transmitter 10 as generally shown in functional block diagrams in FIG. 4. The timing function of the control circuit 50 is implemented by a multivibrator or oscillator 128 which provides a square-wave clock signal whose rate is determined by the variable capacitor 122. The square-wave clock signal is applied therefrom to a divider circuit 130, whose output is applied in turn via a standby switch 124b, which is a portion of the mode sequence switch 124 as generally shown in FIG. 4, to a series of one-shot multivibrators from which the various control signals for effecting the actuation of the RF oscillator 52 are derived to provide RF signal via the antenna switch 56 to the antenna or primary coil 16, whereby similar RF signals are applied to control and energize the receiver 12, as explained above. As seen in FIG. 6, the square-wave clock signal is applied via the standby switch 124b to a first, 10 ms one-shot multivibrator 163 and then to a second 20 ms one-shot multivibrator 165, whose output is applied via a NOR gate 167, NOR gate 182 and an inverter 184 to excite the RF oscillator 52 to provide the 20 ms first power pulse to the receiver 12. Further, the output of the 20 ms one-shot multivibrator 165 is also applied to a 1 ms one-shot multivibrator 132 and then to a one-shot multivibrator 134, from whose Q output terminal a 1 ms pulse is applied via a closed, atrial control switch 126g, the NOR gate 182 and inverter 184 to energize the RF oscillator 52 to provide the first command pulse. In similar fashion, the Q output of the one-shot multivibrator 134 is applied to a further one-shot multiplier 136, whose Q output in turn is applied to a one-shot multiplier 138, whose Q output provides after the 1 ms delay provided by the one-shot multiplier 136, an arming control pulse. The arming control pulse is applied via the NOR gates 174, 176 and 182, and the inverter 184 to the RF oscillator 52 to generate the second command pulse.

In similar fashion, the output of the one-shot multiplier 138 is applied to the inputs of a pair of one-shot multipliers 140 and 142. If the gang connected AV (atrial-ventrical) sequential switch 126e-1 and e-2 are disposed in their uppermost position as seen in FIG. 6, the output of the one-shot multiplier 140 is applied to a ventrical one-shot multiplier 144, whose $\overline{Q}$ output is applied via NOR gates 174 and 176, a closed ventrical switch 126f, and NOR gate 182 to excite the RF oscillator 52 to transmit the third control or ventrical pulse to 32 the receiver 12. If, on the other hand, the switches 126e-1 and e-2 are in their lowermost position and switch 126f is in its open position, the output of the variable, one-shot multiplier 142 actuates the ventrical one-shot multiplier 144 to apply via the NOR gates 174, 176 and 178, the inverter 180 and the closed AV sequential switch 126e-2, whereby the first control or actual pulse and a second control or actual pulse are applied, with a selectable period therebetween as determined by the setting of the potentiometer 120, to excite the RF oscillator 52 for corresponding first and second pulses of RF energy.

In order to operate the transmitter 10 and the receiver 12 in a damand mode, the demand mode control switch 126d is disposed to its lower position (the other switches remaining in the positions shown in FIG. 6), whereby a NOR gate 153 is permitted to respond to a sensed R wave signal as received at a first input of NOR gate 153. In addition, NOR gate 153 may be also enabled by the end of the timing sequence signal as derived from the Q output of the ventrical one-shot multiplier 144. As seen in FIG. 6, the output of the NOR gate 153 energizes a sensing one-shot multivibrator 154 to apply an output via NOR gate 155 to successively energize a 100 ms one-shot multivibrator 150 and a 10 ms one-shot multivibrator 152. The output of the 100 ms one-shot multivibrator 150 is applied through NOR gate 167 and serves to disable the NOR gate 182 for a corresponding period of time and thereby turn on the RF oscillator 52, for a 100 ms period following a delay after a normal patient's heart activity is sensed or when a timing period has been completed. During the 100 ms period, which falls within the refractory period of the patient's heart, the oscillator 52 is turned on and a 100 ms power pulse is transmitted to provide additional power to the receiver 12. The output of the 10 ms multivibrator 152 is applied to a multivibrator 148 whose 1 ms output is applied to the antenna switch 56 to permit the signals as derived from the receiver 12 indicative of the atrial and ventricular signals of the patient's heart and a timing signal, to be applied to he pulse-width modulator 54 and the multiplexer 55, as will be explained with regard to FIG. 7. In similar fashion, a telemetry switch 124a may be closed whereby a one shot multivibrator 156 is energized to provide from its output Q a 4 ms inhibit signal via the NOR gate 158, the inverter 160, the NOR gate 162 and the inverter 164 to the divider circuit 130, whereby the energization of the RF oscillator 52 is terminated for a corresponding period to permit the atrial and ventricular signals as derived from the receiver 12 to be monitored. In a further feature of the timing and mode control circuit 50, a high rate. control switch 126c may be depressed to apply a first signal via the inverter 168 and a second signal via NOR gate 170, NOR gate 162 and inverter 164 to the divider circuit 130, whereby the divider circuit 130 operates to divide the output of the multivibrator 128 by a smaller factor to effect the actuation of the RF oscillator 152 at a higher rate, e.g., by a factor of 4, whereby the patient's heart may be stimulated at the higher rate.

In addition, there is provided a standby switch 124b (as a part of the mode sequence switch 124) which, when disposed in its standby, lower position, applies the output of the divider circuit 130 via an inverter 166 and the NOR gate 155 to excite a 100 ms multivibrator 150, whereby its output is applied via a NOR gate 167, and the NOR gate 182 to excite the RF oscillator 52 for a corresponding period of 100 ms so that only a first power pulse of 100 ms duration is applied to energize the receiver 12.

In a further feature of this invention, a one-shot multivibrator 146 is provided that is responsive to the output of the ventrical one-shot multivibrator 144, to provide at its Q output a signal for a period illustratively of 333 ms to disable the NOR gate 176 thus preventing the application of a ventrical pulse to the patient's heart for a corresponding period. By the provision of the one-shot multivibrator 146, the repeated application of pacing pulses to the patient's ventricular is prevented within the aforementioned period, e.g., 333 ms; thus in the event of a circuit element failure, a higher rate of pacing pulses may not be applied to the patient's ventrical.

Figure 7:
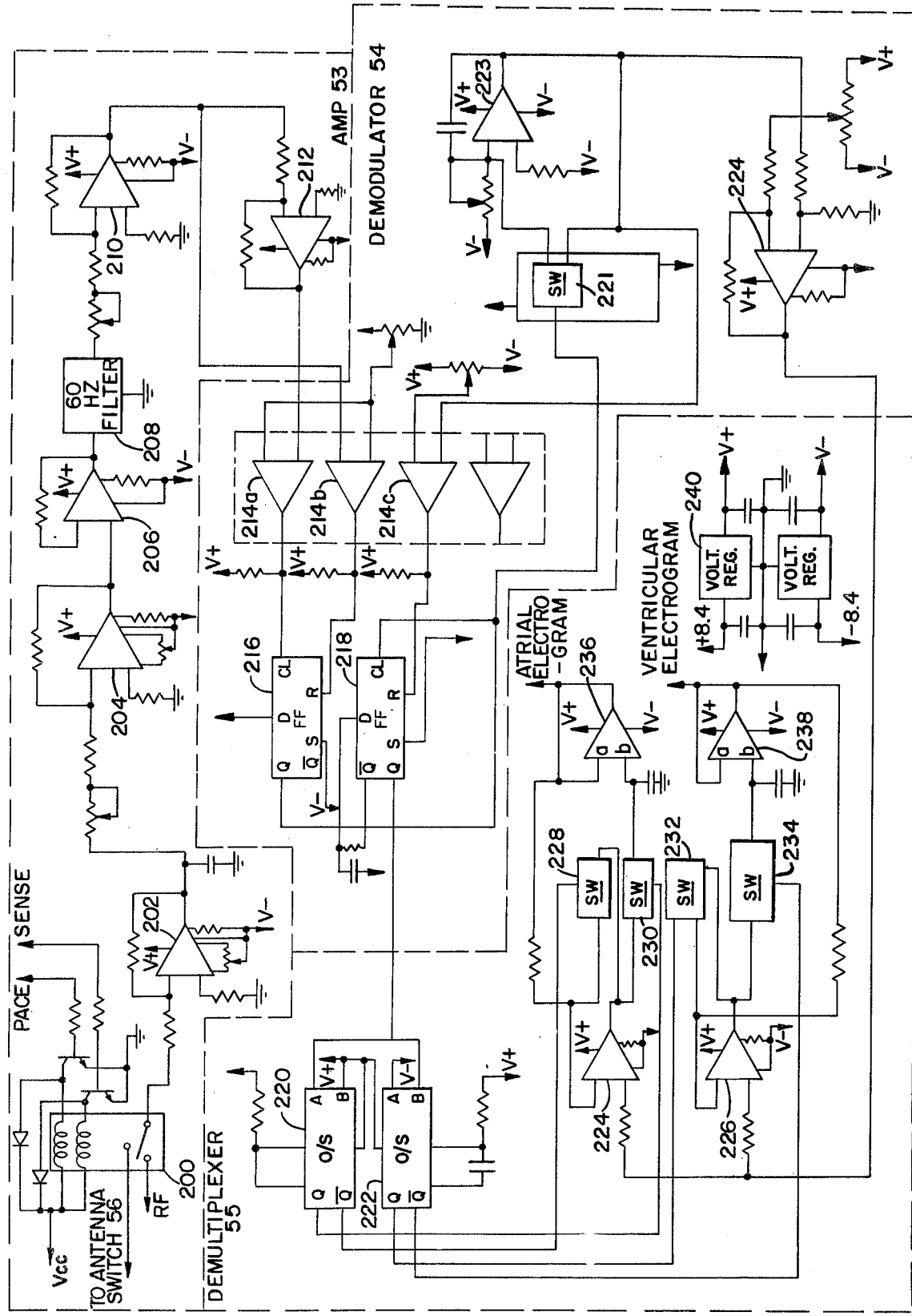

Referring now to FIG. 7, there is shown a detailed schematic circuit diagram of the elements of the pulse-width modulator 54, the amp 53, the antenna switch 56 and the demultiplexer 55. In particular, the antenna switch 56 is comprised of a relay 200 that is responsive to the presence of an RF signal as derived from the RF oscillator 52, to apply the RF signal to the antenna or coil 16 as shown in FIG. 4. In the absence of the RF signal, the relay 200 is thrown to its uppermost position whereby the signals in the form of positive and negative going spikes corresponding to the leading and trailing edges of the pulses transmitted from the transmitter 12 via the antenna 16, are applied to the amp 53 comprised of a plurality of serially connected operational amplifiers 202, 204 and 206. The output of the operational amplifier 206 is applied via a 60 Hz filter 208 to a positive buffer 210 and therefrom to a negative buffer 212. As shown in FIG. 7, the output of the positive buffer 210 is applied to a comparator 214b to be compared with a signal developed by a 50 K potentiometer. In similar fashion, the output of the negative buffer 212 is applied to a comparator 214a to be compared with a signal developed by the 50 K potentiometer. The outputs of the comparators 214a and 214b are applied respectively to the clock (cl) and reset (R) inputs of a flip-flop 216 and have a width corresponding to the aforementioned negative and positive spikes as derived from the coil 16. It is understood that a pulse as generated by the receiver 12 indicative of either an atrial, ventrical or timing signal will appear at the terminals of the coil 16 as the positive and going spikes. In particular, a positive going spike (corresponding to the leading edge of the pulse) above a predetermined level provides an output from the comparator 214b to reset the flip-flop 216, whereas a negative going spike (corresponding to the trailing edge of the pulse) above the predetermined level provides a signal to clock the flip-flop 216.

The pulse as derived from the flip-flop 216 is applied as a clock signal to a second flip-flop 218 for a purpose to be described and also to the demodulator 54, which comprises an a conventional IC. switch 221 which turns on and off in response to its input pulse signal to thereby control the timing period of an integrator essentially comprised of an operational amplifier 223. The output of the operational amplifier 223 is a signal of an amplitude corresponding to the width of the pulse applied to the switch 221. In turn, the output of the operational amplifier 223 is applied to a DC level remover circuit comprised essentially of the operational amplifier 224, whose output has an amplitude that is independent of any DC level and is further applied to the multiplexer 55 to be described.

A further comparator 214c is provided that is responsive to the output of the FET 221 to compare that signal with a reference level whereby an output is developed therefrom in the presence of a timing pulse as derived from the receiver 12 via the antenna 16. It is understood that the timing pulse has a width that is greater than the width of the atrial and ventrical pulses to provide at the output of the FET 221 a signal of greater amplitude, which the comparator 214c recognizes as the timing signal to reset a flip-flop 218. As a result, an output is developed from the Q terminal of the flip-flop 218 to trigger one-shot multivibrators 220 and 222, whose Q and $\overline{Q}$ outputs develop four timing signals to be applied to actuate in timed sequence two distinct sample and hold circuits 236 and 238 corresponding, respectively, to the atrial and ventrical electrograms of the patient. In particular, the Q and $\overline{Q}$ outputs of the flip-flop 220 are applied respectively to switches 228 and 230 to apply at a predetermined time interval an atrial indicating pulse as amplified by amplifier 224 to the sample and hold 236 to provide therefrom a signal whose amplitude is indicative of the patient's atrial electrogram. In similar fashion, the Q and $\overline{Q}$ outputs of the one-shot multivibrator 222 are applied to switches 232 and 234 to apply the ventrical indicating signal as derived from the DC level remover circuit and as amplified by an amplifier 226 to the sample and hold amplifier 238, to provide from its output and a signal indicative of the patient's ventrical electrogram. The switches 228, 230, 232 and 234 may take the form of commercially available IC circuits.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. Cardiac stimulating apparatus for applying stimulating signals to the atria and ventricles of a patient's heart, said cardiac stimulating apparatus comprising:
   a. a first unit disposed externally of the patient's body and including generator means for controlling the generation and transmission of a first power signal and a second control signal in the form of electromagnetic energy into the patient's body and disposed in a timed relation to the first power signal; and
   b. a second unit adapted to be surgically implanted within the patient's body, said second unit including first means responsive to the transmitted first power signal for providing the sole energization of said second unit, and second means for respectively applying the first and second stimulating signals to the atria and ventricles of the patient's heart, said second means includes decoding means responsive to the transmitted second control signal for initiating the operation of and energizing of said second means and controlling the selective application of one of the first and second stimulating signals in accordance with the timed relation of the second control signal.

2. Cardiac stimulating apparatus as claimed in claim 1, wherein said generator means generates the first power signal in the form of a first pulse-like signal having a first relatively long pulse width and the second control signal in the form of first and second pulse-like command signals in first and second sequential time slots following the first pulse-like signal in the timed relation.

3. Cardiac stimulating apparatus as claimed in claim 2, wherein said decoding means comprises means responsive to the trailing edge of the first pulse-like signals for setting first and second timing windows corresponding to the predetermined transmission of the first and second pulse-like signals, and means responsive to receipt of the first and second pulse-like command signals within the corresponding first and second timing windows for applying selectively the first and second stimulating signals to the atria and ventricles of the patient's heart, respectively.

4. Cardiac pacemaker apparatus comprising:
   a. a first unit disposed externally of the patient's body and including generator means for transmitting electro-magnetic energy within the patient's body and including a first power signal and a second control signal, said generator means generates the first power signal in the form of a first pulse-like signal having a first relatively long pulse width, and the second control signal in the form of first and second pulse-like signals in first and second sequential time slots following the first pulse-like signals; and
   b. a second unit adapted to be surgically implanted within the patient's body and comprising first and second electrodes coupled to stimulate different first and second portions of the patient's heart, said second unit including first means responsive solely to the first power signal for providing the sole energization of said second unit, and second means responsive to the command signal for applying selectively first and second stimulating pulses to said first and second electrodes.

5. Cardiac pacemaker apparatus as claimed in claim 4, wherein said second unit comprises decoding means including means responsive to the trailing edge of the first pulse-like signal for establishing first and second timing windows corresponding to the predetermined transmission of the first and second pulse-like signals within the corresponding first and second timing windows for applying selectively the first and second stimulating pulses to the patient's heart.

* * * * *